US006124510A

United States Patent [19]

Elsheikh et al.

[11] Patent Number: 6,124,510

[45] **Date of Patent: *Sep. 26, 2000**

[54] 1234ZE PREPARATION

[75] Inventors: Maher Y. Elsheikh, Tredyffrin; Paul D. Fellenger, Salisbury, both of Pa.

[73] Assignee: Elf Atochem North America, Inc., Philadelphia, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 09/119,560

[22] Filed: Jul. 21, 1998

[51] Int. Cl.[7] .................... C07C 17/00

[52] U.S. Cl. .................... 570/156

[58] Field of Search .................... 570/157, 158

[56] References Cited

U.S. PATENT DOCUMENTS

| | | | |
|---|---|---|---|
| 2,461,523 | 2/1949 | Coffman | 570/156 |
| 3,499,048 | 3/1970 | Regan . | |
| 3,579,595 | 5/1971 | Regan . | |
| 5,986,151 | 11/1999 | Van der Puy . | |

FOREIGN PATENT DOCUMENTS

| | | | |
|---|---|---|---|
| 1754697 A1 | 8/1992 | U.S.S.R. | 570/157 |

OTHER PUBLICATIONS

Knunyants et al, "Reactions of Fluoro Olefins," pp. 1312–1317, 1960.

DePuy et al, "Electronic Effects in Elimination Reactions", pp. 878–881, 1974.

*Primary Examiner*—Alan Siegel

[57] ABSTRACT

Preparation of cis/trans 1234ze monomer is provided, by dehydrofluorination of 245fa using an alkaline solution or using a gas phase catalyzed process.

3 Claims, No Drawings

1234ZE PREPARATION

BACKGROUND OF THE INVENTION

This invention relates to preparation of cis/trans 1,1,1,3-tetrafluoropropene ("1234ze"), a monomer useful for the preparation of various homopolymers and copolymers, particularly to processes for the dehydrofluorination of 1,1,1,3,3-pentafluoropropane ("245fa"), a known blowing agent, to 1234ze using a chromium-based catalyst or a strong base. While the prior art, R. N. Haszeldine, J. Chem. Soc., 1952 (3490), describes the synthesis of cis/trans 1,1,1,3-tetrafluoropropene by fluorination of 1,1,1-trifluoro-2-propyne, this latter feed stock material is not available commercially.

BRIEF SUMMARY OF THE INVENTION

Herein provided is a process for the preparation of 1234ze which comprises (a) contacting 245fa with an alkaline solution or with a chromium-based catalyst, and (b) recovering cis/trans 1,1,1,3-tetrafluoro-2-propene from the resulting reaction mixture.

DETAILED DESCRIPTION

It has now been discovered that the cis and trans isomers of 1,1,1,3-tetrafluoro-2-propene (1234ze) can be conveniently prepared by dehydrofluorination of the blowing agent, 245fa, using either a strong base (either an aqueous or alcoholic solution) or a chromium-based catalyst.

The catalyzed process is preferably carried out in the gas phase. Use of an oxygen-containing gas such as air is desired to extend the catalyst lifetime, the level of oxygen generally being from about 1 to about 10 volume percent (preferably about 2 to 5%), based on the volume of the organic feed. Temperatures of from about 100° C. to about 600° C. are typically used, preferably from about 300° C. to about 400° C. The pressure can be atmospheric. Contact time (total flow rate per catalyst volume) is typically from about 1 to about 60 seconds, preferably from about 20 to 50 seconds. The catalyst is a chromium-based catalyst such as fluorided chromium oxide, $Cr_2O_3$, which chromium-based catalyst is either unsupported or supported on a support such as activated carbon, graphite, fluorided graphite or fluorided alumina, the chromium catalyst being used alone or in the presence of a co-catalyst selected from a nickel, cobalt, manganese or zinc salt. Two such preferred chromium catalysts are high surface area chromium oxide and chromium/nickel on fluorided alumina ($Cr/Ni/AlF_3$), preparation of this latter catalyst being taught, for example, in European Patent 486333. The chromium-based catalysts are preferably activated before use, typically by a procedure wherein the catalyst bed is heated to about 370–380° C. (normally with a continuous flow of nitrogen), after which a mixture of approximately equal volumes of HF and air or nitrogen (preferably nitrogen) are fed over the catalyst bed for about 18 hours.

The dehydrofluorination can also be accomplished using an alkaline solution of a strong base, such as an aqueous or alcoholic solution of potassium hydroxide (KOH), sodium hydroxide (NaOH), calcium hydroxide ($Ca(OH)_2$) or magnesium hydroxide ($Mg(OH)_2$). For the alcoholic solution, a conventional alcohol such as ethanol can be used. The solution typically is from about 0.01 to about 10 molar, preferably 0.1 to 5 molar. The dehydrofluorination is typically conducted at a temperature of from about 20° C. to about 100° C., preferably from about 20° C. to about 50° C.

The following examples are illustrative.

EXAMPLE 1

52.4 Grams of a high surface area $Cr_2O_3$ catalyst was activated by first feeding 30 ccm of nitrogen for 2 hours at 370° C., followed by cofeeding 30 ccm of HF and 30 ccm of nitrogen for 18 hours at 370° C. Subsequently, a mixture of 20 ccm of 245fa and 3 ccm of air (equal to about 3 volume % of oxygen, based on the 245fa volume) was fed over the catalyst bed at 400° C. for a contact time of 45 seconds. Conversion was 96.2%. Selectivity for the desired (1234ze) product was about 96.3% (about 18.5% cis, about 77.8% trans). Performance of the catalyst was steady for 360 hours.

EXAMPLE 2

Example 1 was repeated using $Cr/Ni/AlF_3$ catalyst (activated at 370° C. using a cofeed of 30 ccm of nitrogen and 30 ccm of HF for 18 hours) in a series of 3 tests, using the same temperature and air/245fa feed ratio, but with the contact time between 26 and 39 seconds. Conversions ranged from 88 to 94.5%. Selectivity for the desired (1234ze) product ranged from 96.2 to 98.5% (17.7 to 20.5% cis, 77 to 80.5% trans).

EXAMPLE 3

10 ccm of 245fa was bubbled through 3000 ml of 2.7 molar KOH solution at room temperature (about 20° C.). Analysis of the gaseous dry product, using gas chromatography on line, showed 26% conversion, with selectivity for the desired (1234ze) product of 97.9% (23.9% cis, 74% trans).

What is claimed is:

1. A process for the preparation of cis/trans 1,1,1,3-tetrafluoro-2 -propene which comprises (a) contacting 1,1,1,3,3-pentafluoropropane with an oxygen-containing gas in the presence of a fluorided catalyst selected from $Cr_2O_3$ or $Cr/Ni/AlF_3$, and (b) recovering cis/trans 1,1,1,3-tetrafluoro-2-propene from the resulting reaction mixture.

2. A process as in claim 1 wherein the catalyst is fluorided $Cr_2O_3$.

3. A process as in claim 1 wherein the catalyst is fluorided $Cr/Ni/AlF_3$.

* * * * *